(12) United States Patent
Tukker et al.

(10) Patent No.: US 10,534,274 B2
(45) Date of Patent: Jan. 14, 2020

(54) METHOD OF INSPECTING A SUBSTRATE, METROLOGY APPARATUS, AND LITHOGRAPHIC SYSTEM

(71) Applicant: ASML Netherlands B.V., Veldhoven (NL)

(72) Inventors: Teunis Willem Tukker, Eindhoven (NL); Amandev Singh, Eindhoven (NL); Gerbrand Van Der Zouw, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 78 days.

(21) Appl. No.: 15/723,820

(22) Filed: Oct. 3, 2017

(65) Prior Publication Data

US 2018/0107124 A1 Apr. 19, 2018

(30) Foreign Application Priority Data

Oct. 14, 2016 (EP) .................................... 16193944

(51) Int. Cl.
  *G03F 7/20* (2006.01)
  *G01B 11/27* (2006.01)
  (Continued)

(52) U.S. Cl.
  CPC ..... *G03F 7/70633* (2013.01); *G01B 9/02016* (2013.01); *G01B 11/272* (2013.01);
  (Continued)

(58) Field of Classification Search
  CPC ............ G01N 21/9501; G01N 21/956; G01N 21/95607; G01B 9/02016; G01B 11/272;
  (Continued)

(56) References Cited

U.S. PATENT DOCUMENTS 9,625,836 B2 4/2017 Yamaguchi et al.
2004/0042014 A1 3/2004 Feldman
(Continued)

FOREIGN PATENT DOCUMENTS

JP S63200042 A 8/1988
TW 201504771 A 2/2015
(Continued)

OTHER PUBLICATIONS

International Search Report and Written Opinion of the International Searching Authority directed to related International Patent Application No. PCT/EP2017/074618, dated Dec. 14, 2017; 9 pages.

*Primary Examiner* — Michael A Lyons
(74) *Attorney, Agent, or Firm* — Sterne, Kessler, Goldstein & Fox P.L.L.C.

(57) ABSTRACT

Metrology apparatus and methods for inspecting a substrate are disclosed. A source beam of radiation emitted by a radiation source is split into a measurement beam and a reference beam. A first target on the substrate is illuminated with the measurement beam. A second target separated from the substrate is illuminated with the reference beam. First scattered radiation collected from the first target and second scattered radiation collected from the second target are delivered to the detector. The first scattered radiation interferes with the second scattered radiation at the detector. The first target comprises a first pattern. The second target comprises a second pattern, or a pupil plane image of the second pattern. The first pattern is geometrically identical to the second pattern, the first pattern and the second pattern are periodic and a pitch of the first pattern is identical to a pitch of the second pattern, or both.

18 Claims, 5 Drawing Sheets

(51) Int. Cl.
*G01N 21/956* (2006.01)
*G01B 9/02* (2006.01)
*G01N 21/95* (2006.01)

(52) U.S. Cl.
CPC ....... *G01N 21/9501* (2013.01); *G01N 21/956* (2013.01); *G01N 21/95607* (2013.01); *G03F 7/70625* (2013.01); *G03F 7/70941* (2013.01); *G01N 2021/95676* (2013.01)

(58) Field of Classification Search
CPC ............. G03F 7/70625; G03F 7/70633; G03F 7/70941
See application file for complete search history.

(56) References Cited

U.S. PATENT DOCUMENTS

| | | |
|---|---|---|
| 2006/0033921 A1 | 2/2006 | Den Boef et al. |
| 2007/0030477 A1 | 2/2007 | Hwang et al. |
| 2007/0258086 A1* | 11/2007 | Bleeker .............. G01N 21/4738 356/237.4 |
| 2010/0149548 A1 | 6/2010 | Shmarev et al. |
| 2010/0201963 A1 | 8/2010 | Cramer et al. |
| 2010/0328655 A1 | 12/2010 | Den Boef |
| 2011/0027704 A1 | 2/2011 | Cramer et al. |
| 2011/0043791 A1 | 2/2011 | Smilde et al. |
| 2011/0069292 A1 | 3/2011 | Den Boef |
| 2012/0044470 A1 | 2/2012 | Smilde et al. |
| 2012/0123581 A1 | 5/2012 | Smilde et al. |
| 2013/0258310 A1 | 10/2013 | Smilde et al. |
| 2013/0271740 A1 | 10/2013 | Quintanilha |
| 2013/0278938 A1 | 10/2013 | Fukui et al. |
| 2014/0139814 A1 | 5/2014 | Cramer et al. |
| 2015/0177166 A1* | 6/2015 | Cramer ............... G03F 7/70625 355/67 |
| 2015/0204662 A1* | 7/2015 | Kobayashi ......... G01B 11/2513 356/610 |
| 2016/0025992 A1* | 1/2016 | Van Der Zouw ........................... G01N 21/8806 250/216 |

FOREIGN PATENT DOCUMENTS

| | | |
|---|---|---|
| WO | WO 2012/126718 A1 | 9/2012 |
| WO | WO 2013/178422 A1 | 12/2013 |
| WO | WO 2014/082938 A1 | 6/2014 |
| WO | WO 2016/124399 A1 | 8/2016 |

* cited by examiner

METHOD OF INSPECTING A SUBSTRATE, METROLOGY APPARATUS, AND LITHOGRAPHIC SYSTEM

FIELD

The present invention relates to a method of inspecting a substrate, a metrology apparatus and a lithographic system.

BACKGROUND

A lithographic process is one that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. Stepping and/or scanning movements can be involved, to repeat the pattern at successive target portions across the substrate. It is also possible to transfer the pattern from the patterning device to the substrate by imprinting the pattern onto the substrate.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay (the accuracy of alignment between patterns formed in different patterning steps, for example between two layers in a device) and defocus of the lithographic apparatus. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and principal component analysis.

Methods and apparatus for determining structure parameters are, for example, disclosed in WO 20120126718. Methods and scatterometers are also disclosed in US20110027704A1, US2006033921A1 and US2010201963A1. The targets used by such scatterometers are relatively large gratings, e.g., 40 µm by 40 µm gratings, and the measurement beam generates an illumination spot that is smaller than the grating (i.e., the grating is underfilled). In addition to scatterometry to determine parameters of a structure made in one patterning step, the methods and apparatus can be applied to perform diffraction-based overlay measurements.

Diffraction-based overlay metrology using dark-field image detection of the diffraction orders enables overlay measurements on smaller targets. These targets can be smaller than the illumination spot and may be surrounded by product structures on a wafer. Multiple targets can be measured in one image. Examples of dark-field imaging metrology can be found in international patent applications US2010328655A1 and US2011069292A1 which documents are hereby incorporated by reference in their entirety. Further developments of the technique have been described in published patent publications US20110027704A, US20110043791A, US20120044470A, US20120123581A, US20130258310A, US20130271740A and WO2013178422A1. The above documents generally describe measurement of overlay though measurement of asymmetry of targets. Methods of measuring dose and focus of a lithographic apparatus using asymmetry measurements are disclosed in documents WO2014082938A1 and US2014/0139814A1, respectively. The contents of all the mentioned applications are also incorporated herein by reference.

Stray radiation can reduce the quality, and by extension the accuracy, of optical measurements used in metrology. This reduction in accuracy can reduce the precision of the lithographic apparatus, thereby negatively impacting the precision of components produced by the apparatus, in particular in systems where the detected radiation intensities are very low.

One source of stray radiation in a metrology apparatus is unwanted reflections from surfaces of components that are part of the optical system, e.g. from tiny imperfections on the surfaces of optical components (such as mirrors or aperture stops), as well as multiple reflections off optical surfaces such as lenses. This is particularly problematic in complex lens systems, such as used in lithographic apparatuses, which contain a large number of lenses. In such systems, even a small fraction of reflected stray radiation may compound into a significant source of stray radiation and optical noise. A further source of stray radiation is radiation reflected from interior surfaces of the apparatus that are not part of the optical system, e.g. from other optical systems used for other purposes that are also housed within the metrology apparatus. A further source of stray radiation is radiation reflected off parts of the substrate other than the measurement target itself (e.g. nearby components on the substrate). Yet a further source of stray radiation is foreign particles within the system, such as microscopic dust particles floating inside the apparatus or on an optical surface.

Stray radiation can broadly be classed into two types:

a. directional stray radiation, which is e.g. caused by radiation being reflected multiple times from various surfaces either part of the optical system or not part of the optical system. For example, stray radiation reflections from glass surfaces in the optical system, such as lenses used to shape the beams, can be considered to be directional stray radiation.

b. non-directional stray radiation, which is radiation that is randomly scattered by rough surfaces, or by foreign particles, such as dust, inside the apparatus.

Conventionally, stray radiation in an optical system is reduced by use of suitable anti-reflection coatings, as well as use of apertures and stops at appropriate places in the optical path of the system. However, anti-reflection coatings may only reduce the amount of stray radiation, rather than remove it entirely. In complex optical systems, such as lens systems used in lithographic apparatuses, the compound effect of stray radiation being reflected off each lens surface may be significant. Furthermore, as described above, aperture stops may themselves be sources of stray radiation due to small imperfections in their surfaces, for example due to imperfections in their manufacturing process or by having become damaged.

Scattering from structures on the substrate that are not part of an intended metrology target, for example product structures, may also contribute significantly to noise.

SUMMARY

It is desirable to provide methods and apparatus that can inspect a substrate accurately and reliably even in the presence of stray radiation and other sources of noise.

According to an aspect of the invention, there is provided a method of inspecting a substrate, the method comprising: splitting a source beam of radiation emitted by a radiation source into a measurement beam and a reference beam; illuminating a first target with the measurement beam, the first target being on the substrate; illuminating a second target with the reference beam, the second target being separated from the substrate; collecting first scattered radiation from the first target and delivering the first scattered radiation to a detector; and collecting second scattered radiation from the second target and delivering the second scattered radiation to the detector, wherein: the first scattered radiation interferes with the second scattered radiation at the detector; the first target comprises a first pattern; the second target comprises a second pattern, or a pupil plane image of the second pattern; and the first pattern is geometrically identical to the second pattern, or the first pattern and the second pattern are periodic and a pitch of the first pattern is identical to a pitch of the second pattern.

According to an aspect of the invention, there is provided a metrology apparatus for inspected a substrate, the metrology apparatus comprising: a radiation source configured to provide a source beam of radiation; a beam splitter configured to split the source beam of radiation into a measurement beam and a reference beam; and an optical system configured to: illuminate a first target with the measurement beam, the first target being on the substrate; illuminate a second target with the reference beam, the second target being separated from the substrate; collect first scattered radiation from the first target and deliver the first scattered radiation to a detector; and collect second scattered radiation from the second target and deliver the second scattered radiation to the detector, wherein: the optical system is configured such that the second scattered radiation is delivered to the detector in such a way as to interfere with the first scattered radiation at the detector; the first target comprises a first pattern; the second target comprises a second pattern, or a pupil plane image of the second pattern; and the first pattern is geometrically identical to the second pattern, or the first pattern and the second pattern are periodic and a pitch of the first pattern is identical to a pitch of the second pattern.

It should be noted that the embodiments of the invention as described above, and in the following, are applicable in any apparatus wherein optical measurements are performed. In particular, the embodiments are applicable to any methods or apparatuses which form part of a lithographic process, wherein optical measurements are performed on targets (e.g. periodic targets such as diffraction gratings). Exemplary applications include, without limitation: measuring overlay in a metrology apparatus (which may also be referred to as an inspection apparatus); focus control; measurement of critical dimension (CD); or measuring the form of a target (such as side wall angle (SWA) or bottom tilt). In exemplary applications, the parameter determined includes, without limitation, overlay, CD, focus, SWA or bottom tilt.

These and further features and advantages of the invention will be apparent to the skilled reader from a consideration of the detailed description of examples that follows.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Before describing such embodiments in more detail, however, it is instructive to present an example environment in which embodiments of the present invention may be implemented.

Figure 1:
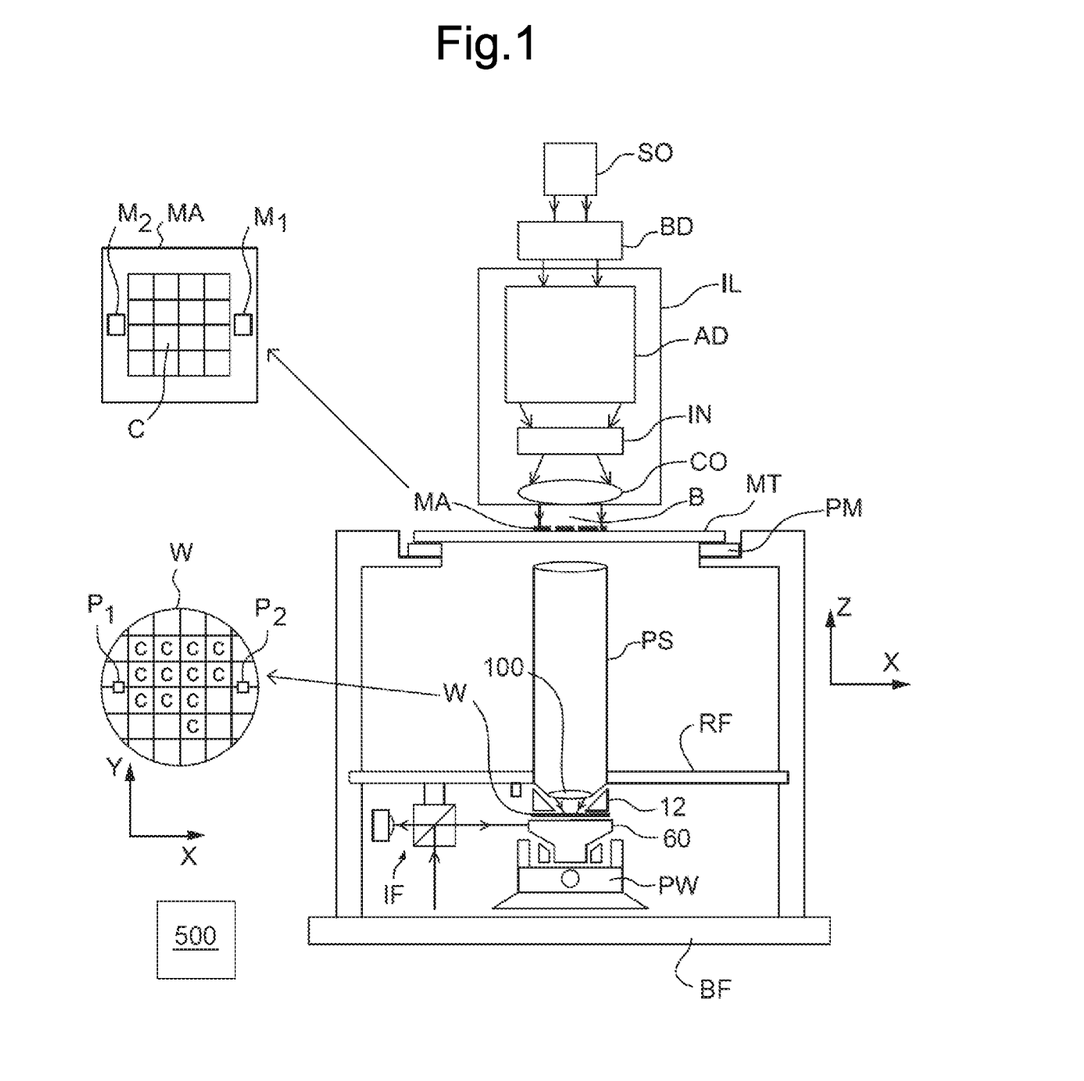
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a support structure (e.g., a mask table) MT constructed to support a patterning device (e.g., a mask) MA and connected to a first positioner PM configured to accurately position the patterning device in accordance with certain parameters, a substrate table (e.g., a wafer table) WT constructed to hold a substrate (e.g., a resist coated wafer) W and connected to a second positioner PW configured to accurately position the substrate in accordance with certain parameters, and a projection system (e.g., a refractive projection lens system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic, or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing various types of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system."

In this embodiment, for example, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables and, for example, two or more mask tables. In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (which are commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam to have a desired uniformity and intensity distribution in its cross section.

The radiation beam B is incident on the patterning device (e.g., mask MA), which is held on the support structure (e.g., mask table MT), and is patterned by the patterning device. Having traversed the mask MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
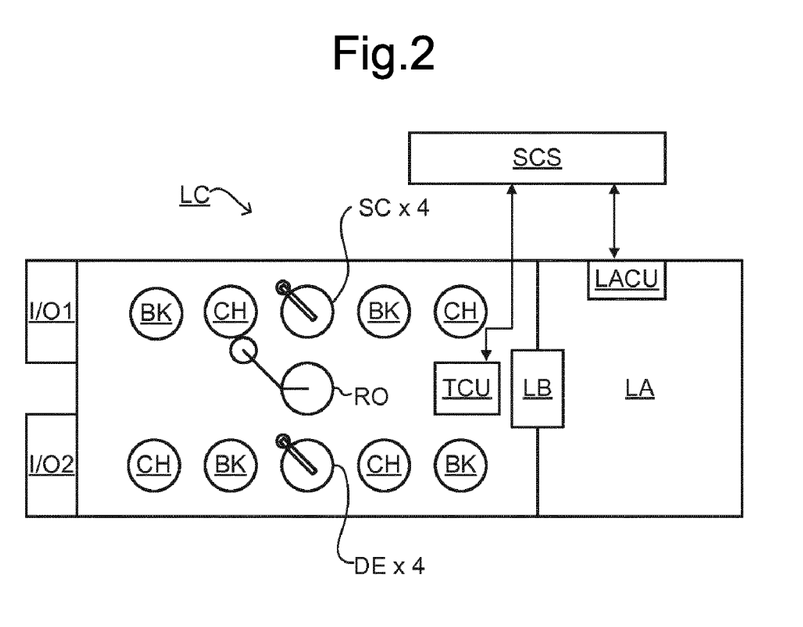
FIG. 2 depicts a lithographic cell or cluster.

As shown in FIG. 2 the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports 1/01, 1/02, moves them between the different process apparatus and delivers then to the loading bay LB of the lithographic apparatus. These devices, which are often collectively referred to as the track, are under the control of a track control unit TCU that is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments, for example, can be made to exposures of subsequent substrates, especially if the inspection can be done soon and fast enough that other substrates of the same batch are still to be exposed. Also, already exposed substrates may be stripped and reworked to improve yield, or possibly be discarded, thereby avoiding performing exposures on substrates that are known to be faulty. In a case where only some target portions of a substrate are faulty, further exposures can be performed only on those target portions that are deemed to be non-faulty.

A metrology apparatus (which may also be referred to as an inspection apparatus) is used to determine the properties of the substrates, and in particular, how the properties of different substrates or different layers of the same substrate vary from layer to layer. The metrology apparatus may be integrated into the lithographic apparatus LA or the lithocell LC or may be a stand-alone device. To enable most rapid measurements, it is desirable that the metrology apparatus measure properties in the exposed resist layer immediately after the exposure. However, the latent image in the resist has a very low contrast, as in there is only a very small difference in refractive index between the parts of the resist which have been exposed to radiation and those which have not—and not all metrology apparatus have sufficient sensitivity to make useful measurements of the latent image. Therefore measurements may be taken after the post-exposure bake step (PEB) that is customarily the first step carried out on exposed substrates and increases the contrast between exposed and unexposed parts of the resist. At this stage, the image in the resist may be referred to as semi-latent. It is also possible to make measurements of the developed resist image, at which point either the exposed or unexposed parts of the resist have been removed, or after a pattern transfer step such as etching. The latter possibility limits the possibilities for rework of faulty substrates but may still provide useful information.

Figure 3A:
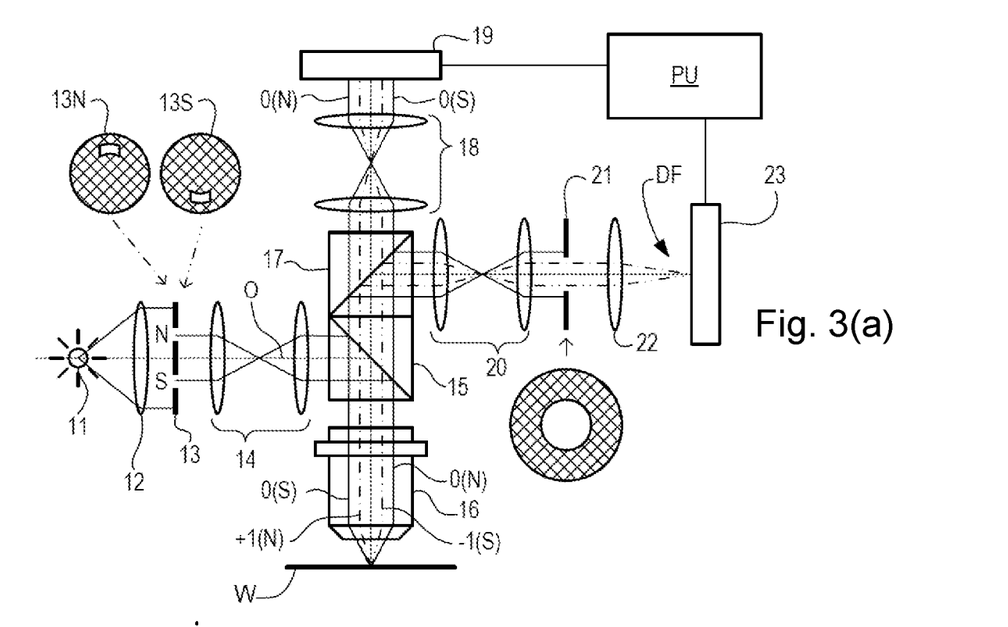
FIGS. 3(a)-3(d) comprises 3(a) a schematic diagram of a dark field scatterometer for use in measuring targets using a first pair of illumination apertures; 3(b) a detail of a diffraction spectrum of a target grating for a given direction of illumination; 3(c) a depiction of a known form of multiple grating target and an outline of a measurement spot on a substrate; and 3(d) a depiction of an image of the target of FIG. 3(c) obtained in the scatterometer of FIG. 3(a)

A metrology apparatus is shown in FIG. 3(a). A target T and diffracted rays of measurement radiation used to illuminate the target are illustrated in more detail in FIG. 3(b). The metrology apparatus illustrated is of a type known as a dark field metrology apparatus. The metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, light emitted by source 11 (e.g., a xenon lamp) is directed onto substrate W via a beam splitter 15 by an optical system comprising lenses 12, 14 and objective lens 16. These lenses are arranged in a double sequence of a 4F arrangement. A different lens arrangement can be used, provided that it still provides a substrate image onto a detector, and simultaneously allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures. The rest of the pupil plane is desirably dark as any unnecessary light outside the desired illumination mode will interfere with the desired measurement signals.

Figure 3B:
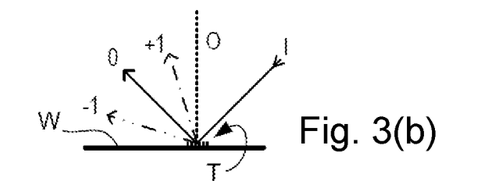

As shown in FIG. 3(b), target T is placed with substrate W normal to the optical axis O of objective lens 16. The substrate W may be supported by a support (not shown). A ray of measurement radiation I impinging on target T from an angle off the axis O gives rise to a zeroth order ray (solid line 0) and two first order rays (dot-chain line+1 and double dot-chain line−1). It should be remembered that with an overfilled small target, these rays are just one of many parallel rays covering the area of the substrate including metrology target T and other features. Since the aperture in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the grating pitches of the targets and the illumination angles can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target T on substrate W are collected by objective lens 16 and directed back through beam splitter 15. Returning to FIG. 3(a), both the first and second illumination modes are illustrated, by designating diametrically opposite apertures labeled as north (N) and south (S). When the incident ray I of measurement radiation is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16.

A second beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for many measurement purposes such as reconstruction.

In the second measurement branch, optical system 20, 22 forms an image of the target T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. The images captured by sensors 19 and 23 are output to processor PU which processes the image, the function of which will depend on the particular type of measurements being performed. Note that the term 'image' is used here in a broad sense. An image of the grating lines as such will not be formed, if only one of the −1 and +1 orders is present.

The particular forms of aperture plate 13 and field stop 21 shown in FIG. 3 are purely examples. In another embodiment of the invention, on-axis illumination of the targets is used and an aperture stop with an off-axis aperture is used to pass substantially only one first order of diffracted light to the sensor. In yet other embodiments, $2^{nd}$, $3^{rd}$ and higher order beams (not shown in FIG. 3) can be used in measurements, instead of or in addition to the first order beams.

In order to make the measurement radiation adaptable to these different types of measurement, the aperture plate 13 may comprise a number of aperture patterns formed around a disc, which rotates to bring a desired pattern into place. Note that aperture plate 13N or 13S can only be used to measure gratings oriented in one direction (X or Y depending on the set-up). For measurement of an orthogonal grating, rotation of the target through 90° and 270° might be implemented. The use of these, and numerous other variations and applications of the apparatus are described in prior published applications, mentioned above.

Figure 3C:
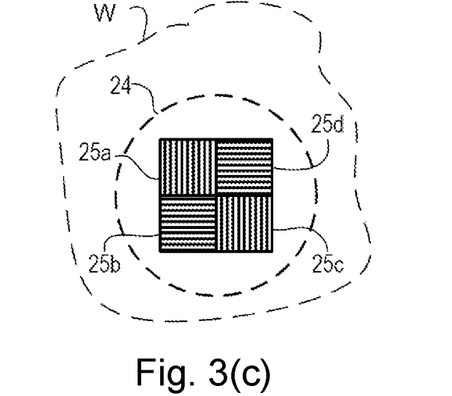

FIG. 3(c) depicts a (composite) target formed on a substrate according to known practice. The target in this example comprises four gratings 25a to 25d positioned closely together so that they will all be within a measurement scene or measurement spot 24 formed by the metrology radiation illumination beam of the metrology apparatus. The four gratings thus are all simultaneously illuminated and simultaneously imaged on sensors 19 and 23. In an example dedicated to measurement of overlay, gratings 25a to 25d are themselves composite gratings formed by overlying gratings that are patterned in different layers of the semi-conductor device formed on substrate W. Gratings 25a to 25d may have differently biased overlay offsets (deliberate mismatch between layers) in order to facilitate measurement of overlay between the layers in which the different parts of the composite gratings are formed. Such techniques are well known to the skilled person and will not be described further. Gratings 25a to 25d may also differ in their orientation, as shown, so as to diffract incoming radiation in X and Y directions. In one example, gratings 25a and 25c are X-direction gratings with biases of the +d, −d, respectively. Gratings 25b and 25d are Y-direction gratings with offsets +d and −d respectively. Separate images of these gratings can be identified in the image captured by sensor 23. This is only one example of a target. A target may comprise more or fewer than four gratings, or only a single grating.

Figure 3D:
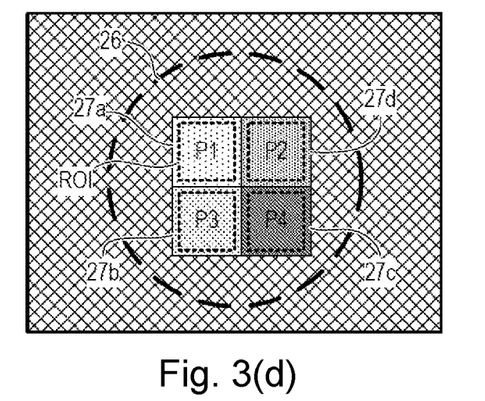

FIG. 3(d) shows an example of an image that may be formed on and detected by the sensor 23, using the target of FIG. 3(c) in the apparatus of FIG. 3(a). While the pupil plane image sensor 19 cannot resolve the different individual gratings 25a to 25d, the image sensor 23 can do so. The dark rectangle represents the field of the image on the sensor, within which the illuminated spot 24 on the substrate is imaged into a corresponding circular area 26. Within this, rectangular areas 27a to 27d represent the images of the small target gratings 25a to 25d. If the targets are located in product areas, product features may also be visible in the periphery of this image field. Image processor and controller PU processes these images using pattern recognition to identify the separate images 27a to 27d of gratings 25a to 25d. In this way, the images do not have to be aligned very precisely at a specific location within the sensor frame, which greatly improves throughput of the measuring apparatus as a whole.

Once the separate images of the gratings have been identified, the intensities of those individual images can be measured, e.g., by averaging or summing selected pixel intensity values within the identified areas. Intensities and/or other properties of the images can be compared with one another. These results can be combined to measure different parameters of the lithographic process. Overlay performance is an important example of such a parameter.

The performance of the metrology apparatus depends on the quality of its optical measurements. As described in the introductory part of the description, the quality of the optical measurements can be negatively affected by various sources of stray radiation. Certain effects of stray radiation may be referred to as ghosting. Stray radiation undesirably reduces signal to noise. Noise may also arise due to unwanted scattering from product structures adjacent to metrology targets, which may further reduce signal to noise.

In an embodiment, a method of inspecting a substrate W using a metrology apparatus is provided. The method and metrology apparatus improve signal to noise by rejecting noise associated with stray radiation, scattering from product structures, and/or other sources of noise.

Figure 4:
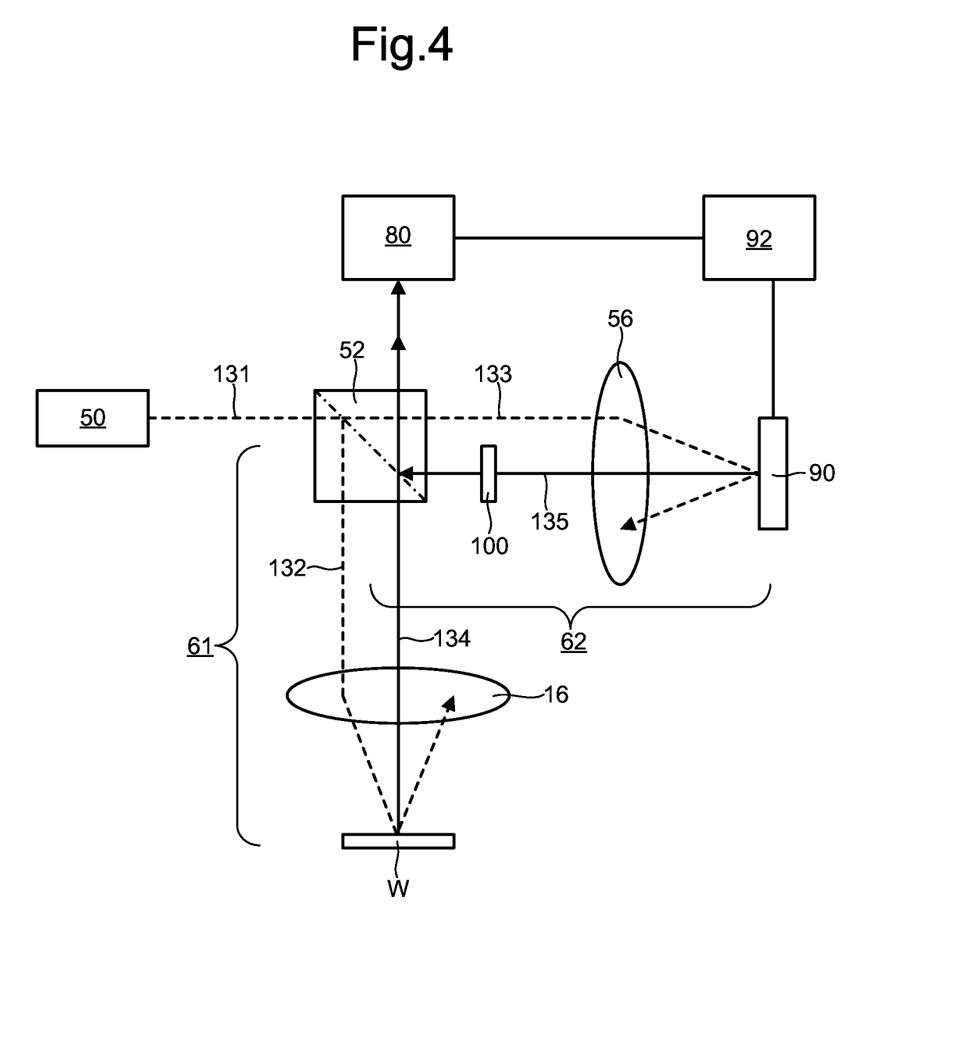
FIG. 4 depicts a metrology apparatus according to an embodiment.

An embodiment of the metrology apparatus is depicted schematically in FIG. 4.

Illumination radiation is depicted by broken lines. Diffracted radiation is depicted by solid lines. The method comprises splitting a source beam 131 emitted by a radiation source 50 into a measurement beam 132 and a reference beam 133. The splitting is performed by beam splitter 52. A first target is illuminated by the measurement beam 132. The first target is provided on the substrate W. A second target is illuminated by the reference beam 133. The second target is separated from the substrate W (i.e. is not provided on the substrate W). In an embodiment, the second target is provided by a spatial light modulator 90 (SLM). In an embodiment the SLM 90 forms a phase grating. As will be described below, the second target needs to provide a pattern that matches a pattern of the first target. An SLM is able to provide this matching flexibly for plural different first targets. Thus, when measurement of a different first target is required, the same SLM 90 can be used to generate a suitable second target. However, it is not essential for the second target to be provided by an SLM. In other embodiments, the second target is provided by a fixed structure. If the first target changes the fixed structure can be replaced by a different fixed structure comprising a second target that is suitable for the new first target.

First scattered radiation 134 is collected from the first target and delivered to a detector 80. Second scattered radiation 135 is collected from the second target and delivered to the detector 80. The first scattered radiation interferes with the second scattered radiation at the detector 80. The detector 80 detects the radiation intensity resulting from the interference. The detector 80 may be configured to detect the radiation intensity resulting from the interference in the image plane or in the pupil plane. The first target comprises a first pattern (e.g. a periodic structure, such as a grating, or an aperiodic structure, such as a structure suitable for measuring critical dimension CD). The second target comprises a second pattern or a pupil plane image of the second pattern. The first pattern is geometrically identical to the second pattern, or the first pattern and the second pattern are periodic and a pitch of the first pattern is identical to a pitch of the second pattern, or both. Where the first pattern and the second pattern are geometrically identical, each shape in the first pattern will have a corresponding shape in the second pattern that is identical in shape, size and orientation, and the relative positions of all shapes in the first pattern will be the same as the relative positions of all shapes in the second pattern. If the first pattern were overlaid on the second pattern, boundary lines of all of the shapes in the first pattern would be coincident with boundary lines defining all of the shapes in the second pattern.

An arrangement is thus provided in which radiation from the same source 50 is split so as to propagate independently through two separate optical branches. A first of the optical branches, which may be referred to as substrate branch 61, comprises the substrate W and the first target on the substrate W. The other optical branch, which may be referred to as a reference branch 62, comprises the second target (e.g. SLM). The substrate branch 61 and the reference branch 62 are configured to operate in the manner of a Michelson interferometer. In an embodiment the reference branch 62 is optically identical to the substrate branch 61 except for the targets in each branch: in the substrate branch the first target is provided on the substrate W whereas in the reference branch the second target is provided separately, for example using an SLM. The substrate branch 61 may comprise an objective lens 16 configured in a similar manner to the objective lens 16 shown in FIG. 3(a). The reference branch 62 in this case would then comprise a lens 56 that is constructed and positioned in a corresponding way to the objective lens 16 (in the case where the second target comprises the second pattern rather than a pupil plane image of the second pattern). In an embodiment, the radiation source 50 comprises components corresponding to one or more of the source 11, optical lenses 12 and 14, and plate 13 of FIG. 3(a). In such an embodiment, and in other embodiments, the detector 80 comprises components corresponding to one or more of the optical system 20, 22, the aperture stop 21, and the sensor 23 of FIG. 3. Thus, the combination of the radiation source 50, beam splitter 52, substrate branch 61 and detector 80 may be implemented using components involved in measurement via the second measurement branch of FIG. 3(a). However, the addition of the reference branch 62 enables higher signal to noise to be achieved than is typically possible using a standard implementation of the second measurement branch of FIG. 3(a). Alternatively or additionally, the detector 80 may be configured to comprise components corresponding to the optical system 18 and first sensor 19 of FIG. 3(a), so as to detect a diffraction spectrum (pupil plane image) on the first sensor 19. Thus, the combination of the radiation source 50, beam splitter 52, substrate branch 61 and detector 80 may be implemented using components involved in measurement via the first measurement branch of FIG. 3(a). However, the addition of the reference branch 62 enables higher signal to noise to be achieved than is typically possible using a standard implementation of the first measurement branch of FIG. 3(a).

In an embodiment, the second target comprises the second pattern and an optical path relative to the first target (particularly path length from the first target for each frequency of radiation provided by the radiation source) of the first scattered radiation 134 between the first target and the detector 80 is identical to an optical path relative to the second target (particularly path length from the second target for each frequency of radiation provided by the radiation source) of the second scattered radiation 135 between the second target and the detector 80. In an alternative embodiment in which the second target comprises a pupil plane image of the second pattern, an optical path, relative to the pupil plane image of the first target, of the first scattered radiation 134 between a pupil plane image of the first target and the detector 80 is identical to the optical path, relative to the second target, of the second scattered radiation 135 between the second target and the detector 80. In both cases, the identical optical paths ensure that interference occurs between the radiation from the substrate branch 61 and radiation from the reference branch 62 for all wavelengths of radiation through the system. For different wavelengths of radiation the overall path length through the system will be different, whether the radiation propagates through the substrate branch 61 or the reference branch 62. This is because the diffraction angles, which determine the angle at which a given diffraction order leaves the first target and the second target, depend on the wavelength of the radiation. However, the path length through the substrate branch 61, at least between the pupil plane image in the substrate branch 61 and the detector 80, will be the same as the path length through the reference branch 62, at least between the pupil plane image in the reference branch 62 and the detector 80. This means that interference occurs for all wavelengths of radiation, even in the case where the radiation source 50 has a large bandwidth.

The interference will only occur, however, between radiation that has scattered from the first pattern and the second pattern (or pupil plane image of the second pattern). Only these two source of scattered radiation will be scattered at the correct angle and have the same path length through the system. Other sources of scattered radiation (e.g. stray radiation from ghosting or from product structures adjacent to the first pattern) will not contribute (or will contribute much less) to the interference. The negative influence from unwanted sources of scattered radiation will therefore be reduced or removed, thereby improving the signal to noise ratio that is achieved by the system.

In an embodiment, an outer contour of the first pattern is substantially the same shape, substantially the same size, or substantially the same shape and the same size, as an outer contour of the second pattern. Interference can only occur to a large extent between matching patterns (i.e. patterns that are identical or, for periodic patterns, at least have identical pitch). Arranging for the first pattern and the second pattern to match each other in terms of their outer shape and dimensions increases the amount of wanted radiation that interferes at the detector 80 and contributes to the output signal. Any structures on the substrate that are positioned outside of the region defined by the shape and size of the first pattern will not contribute, as long as corresponding structures are not present in the second target, and are thus effectively (spatially) filtered out. This process may be referred to as spatial filtering.

In an embodiment, signal to noise ratio is improved further using phase sensitive detection. Phase sensitive detection is implemented by apply a time-varying phase modulation to the second scattered radiation. The phase modulation can be applied using an SLM 90 for example. In the example of FIG. 4, a lock-in controller 92 is provided which drives the phase modulation of the SLM 90 and applies lock-in processing to the signal measured by the detector 80. Phase modulating the radiation from the reference branch 62 in this manner makes it possible to use a lock-in detection principle (well known in the art of phase sensitive detection) to extract only components of the radiation detected by the detector 80 that are phase modulated in the same way (i.e. with the same frequency). The phase sensitive detection effectively allows the output from the detector 80 to be filtered based on the frequency of the phase modulation. The contribution from dynamic noise (e.g. detector noise, source noise, environmental noise) is reduced as a function of 1/frequency, where "frequency" is the frequency of the phase modulation applied in the reference branch 62. This effect further reduces the negative influence of stray radiation and enhances the spatial filtering discussed above. Signal to noise is therefore improved.

Additionally, the time-varying phase modulation makes it possible for phase information to be extracted at the detector 80, in addition to intensity. This phase information effectively allows the full electric field to be detected rather than just the intensity, enabling further information about a target on the substrate W to be extracted from the output from the detector. The phase information is obtainable using a process known to the skilled person in this technical area as phase unwrapping.

In the example of FIG. 4, the SLM 90 produces a second pattern in a plane in the reference branch 62 that corresponds to the plane of the first pattern in the substrate branch 61 (i.e. such that path lengths from the first pattern and the second pattern to the detector 80 are equal). As mentioned above, it is also possible to position the SLM 90 at a pupil plane in the reference branch 62 and configure the SLM 90 to form a pattern which corresponds to a diffraction spectrum of the second pattern. In this way, radiation propagating from the SLM 90 towards the detector 80 would be exactly the same as if the SLM 90 was positioned as shown in FIG. 4 and configured to form the second pattern itself rather than the diffraction spectrum. The pattern formed by the SLM 90 can be phase modulated in order to implement phase sensitive detection in the same way. Positioning the SLM 90 in the pupil plane in this manner may desirably alleviate the need for extremely small pixels, relative to the case where the SLM 90 produces the second pattern directly.

Interference is very sensitive to external vibrations. External vibrations can negatively affect the stability of the interference. Phase sensitive detection greatly reduces the sensitivity to vibrations, particularly where the vibrations are outside of the frequency band used for the phase sensitive detection.

The phase sensitive detection can be described mathematically as follows.

The field diffracted from the target (e.g. from the first pattern) on the substrate W is given by $E_S = A_S e^{i(\omega t + \beta_S)}$, where $|E_S| = A_S = \sqrt{\text{substratebranchintensity}}$.

The field diffracted from the corresponding target in the reference branch 62 (e.g. second pattern) is given by $E_{LO} = A_{LO} e^{i(\Omega t + \beta_{LO}(T))}$ where $|E_{LO}| = A_{LO} = \sqrt{\text{preferencebranchintensity}}$.

The value $\beta_S$ is a spatially resolved phase of the diffraction signal originated from the substrate branch 61. The value $\beta_{LO}(T)$ is the spatially resolved phase of the signal originating from the reference branch 62. This phase is modulated at a selected frequency provided by the SLM 90.

The radiation intensity received by the detector 80 may be written as follows:

$$I_{Detector} = |E_{LO}|^2 + |E_S|^2 + 2A_{LO}A_S e^{i(\beta_S - \beta_{LO}(T))} + 2A_{LO}A_S e^{i(2\omega t + \beta_S + \beta_{LO}(T))} + \sum_{\omega=0}^{\omega=\infty} \text{Noise}(\omega)$$

where:

$|E_{LO}|^2$ corresponds to the intensity from the reference branch 62;

$|E_S|^2$ corresponds to the intensity from the substrate branch 61;

$2A_{LO}A_S e^{i(2\omega t + \beta_S \beta_{LO}(T))}$ is a time-varying optical signal in which the frequency is twice the optical frequency (and therefore too fast to register, such that the effective contribution from this term is zero);

$2A_{LO}A_S e^{i(\beta_S - \beta_{LO}(T))}$ is a time varying optical signal varying at the frequency of the phase modulation (this is the signal of interest for the lock-in detection); and $\sum_{\omega=0}^{\omega=\infty} \text{Noise}(\omega)$ is a noise term representing contributions from dynamic noise sources spread over a range of frequencies.

The lock-in processing extracts the following signal:

$$I_{Detector}(\text{lock-in}) = 2A_{LO}A_S e^{i(\beta_S - \beta_{LO}(T))} + \sum_{\omega=\frac{2\pi}{T}}^{\omega=\frac{2\pi}{T}+\Delta\omega} \text{Noise}(\omega)$$

The contribution from the noise is limited to a narrow bandwidth $\Delta\omega$ of the phase modulation and is therefore small. The remaining term $2A_{LO}A_S e^{i(\beta_S - \beta_{LO}(T))}$ therefore provides accurate amplitude and phase information about the diffraction from the target on the substrate (e.g. first pattern).

Figure 5:
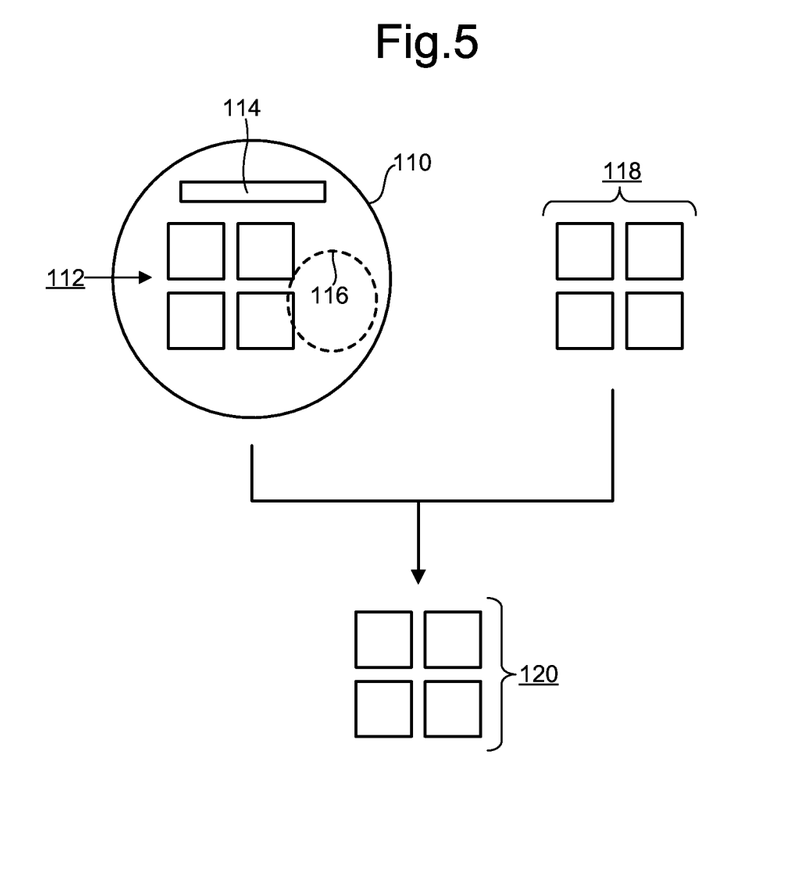
FIG. 5 illustrates lock-in processing of a phase modulated signal.

The process can be visualised as shown in FIG. 5. Radiation is detected within a region of interest 110 (top left) by detector 80. The radiation comprises a contribution 112 from a target on the substrate W. In this example, the contribution 112 comprises radiation in four distinct regions (the four squares), each region corresponding to a different first pattern. The target may be a composite target comprising four biased gratings, as discussed above with reference to FIG. 3(c). The radiation in the region of interest 110 further includes radiation 114 scattered from a product structure adjacent to the target on the substrate W and stray radiation 116 (a ghost pattern for example). The radiation detected by the detector 80 further comprises a contribution 118 (top right) from the reference branch 62 that is phase modulated. The resulting interference pattern and lock-in process provides a signal containing a contribution 120 resulting from interference between the contribution 112 (top left) and the contribution 118 (top right) only. Noise from contributions 114 and 116 (and from other sources, such as vibrations) is removed or reduced both by the spatial filtering provided by the interference technique itself (which favours extraction of signal only where the path lengths are equal: namely in spatial regions where the pattern on the SLM 90 matches the pattern on the target on the substrate W) and by the lock-in processing (which favours extraction of signal only where there is a phase modulation at the frequency of the modulation applied at the SLM 90).

The radiation intensity produced by the interference at the detector 80 may take various forms, depending on the details of the target on the substrate W that is being measured and whether or not a time-varying phase modulation has been applied. The interference may form one or more interference patterns comprising fringes for example, where a time-varying phase modulation has not been applied to radiation components involved in the interference. Alternatively or additionally, one or more regions of uniform intensity may be formed from interference involving components to which a time-varying phase modulation has been applied. Where time-varying phase modulation is used, phase unwrapping may be used to obtain a phase map. In the case of a target such as that described above with reference to FIG. 5, the radiation intensity at the detector 80 may comprise four regions of relatively uniform intensity. In this case the detector 80 could be implemented using a small number of discrete sensors, for example four photodiodes. In other embodiments, the radiation intensity at the detector 80 may comprise more spatial structure and the detector 80 may accordingly be configured to record radiation intensity at a higher spatial resolution (i.e. have more pixels). The detector 80 may comprise a sensor such as the sensor 23 or sensor 19 (e.g. a CCD or CMOS sensor) of FIG. 3(a).

In an embodiment, the method further comprises filtering the second scattered radiation as a function of a signal level of the first scattered radiation in order to control a dynamic range at the detector 80. As described above, the size of the signals of interest is proportional to the product $A_{LO}A_S$, where $A_S$ is a field amplitude associated with radiation from the substrate branch 61 (first scattered radiation) and $A_{LO}$ is a field amplitude associated with radiation from the reference branch 62 (second scattered radiation). By filtering the second scattered radiation it is possible to control $A_{LO}$ and, therefore, the overall signal level $A_{LO}A_S$. The overall signal level can then be controlled to achieve good dynamic range (and therefore high signal to noise ratio). For example, where $A_S$ is found to be relatively high (a bright wafer), the filtering may select a relatively low $A_{LO}$ in order to achieve high signal to noise. Conversely, if $A_S$ falls a higher value for $A_{LO}$ can be selected by appropriate filtering (or removal of the filtering) in order to maintain the same signal to noise ratio or at least an acceptably high signal to noise ratio. The filtering may be implemented in various ways known to the skilled person. In the example shown in FIG. 4, a motorised filter system 100 is provided which comprises a plurality of filters of different strength mounted on a motorised wheel. Rotation of the wheel can selectively bring different filters into the path of radiation in the reference branch 62, thereby providing the required control of the filtering of the second scattered radiation.

In a typical implementation, the phase sensitive detection is expected to improve dynamic range by $10$-$10^2$ due to interferometric noise reduction. The controllable filtering of the second scattered radiation is expected to improve dynamic range by a further $1$-$10^2$. The overall dynamic range enhancement may therefore be in the range of $10$-$10^4$. As an illustration, in comparison to an implementation which does not use phase sensitive detection or control of filtering of the second scattered radiation, if 1 µW of diffracted radiation from the substrate W was found to be necessary to achieve an acceptable signal to noise ratio, in an embodiment which does use phase sensitive detection and control of filtering of the second scattered radiation, it would be possible to achieve the same signal to noise ratio with only 100 nW-0.1 nW of diffracted radiation from the substrate W. The ability to achieve high signal to noise ratio even with very small levels of diffracted light reduces the need to carry out longer measurements (e.g. to integrate the signal longer in order to obtain an adequate signal to noise ratio). Throughput is therefore improved.

The concepts disclosed herein may find utility beyond post-lithography measurement of structures for monitoring purposes. For example, such a detector architecture may be used in future alignment sensor concepts that are based on pupil plane detection, used in lithographic apparatuses for aligning the substrate during the patterning process.

While the targets described above are metrology targets specifically designed and formed for the purposes of measurement, in other embodiments, properties may be measured on targets which are functional parts of devices formed on the substrate. Many devices have regular, grating-like structures. The terms 'target grating' and 'target' as used herein do not require that the structure has been provided specifically for the measurement being performed.

The metrology apparatus can be used in a lithographic system, such as the lithographic cell LC discussed above with reference to FIG. 2. The lithographic system comprises a lithographic apparatus LA that performs a lithographic process. The lithographic apparatus may be configured to use the result of a measurement by the metrology apparatus of a structure formed by the lithographic process when performing a subsequently lithographic process, for example to improve the subsequent lithographic process.

An embodiment may include a computer program containing one or more sequences of machine-readable instructions describing methods of measuring targets on a structures and/or analyzing measurements to obtain information about a lithographic process. There may also be provided a data storage medium (e.g., semiconductor memory, magnetic or optical disk) having such a computer program stored therein. Where an existing lithography or metrology apparatus is already in production and/or in use, the invention can be implemented by the provision of updated computer program products for causing a processor to perform the methods described herein.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains multiple processed layers.

Further embodiments according to the invention are further described in below numbered clauses:

1. A method of inspecting a substrate, the method comprising:
   splitting a source beam of radiation emitted by a radiation source into a measurement beam and a reference beam;
   illuminating a first target with the measurement beam, the first target being on the substrate;
   illuminating a second target with the reference beam, the second target being separated from the substrate;
   collecting first scattered radiation from the first target and delivering the first scattered radiation to a detector; and
   collecting second scattered radiation from the second target and delivering the second scattered radiation to the detector, wherein:
   the first scattered radiation interferes with the second scattered radiation at the detector;
   the first target comprises a first pattern;
   the second target comprises a second pattern, or a pupil plane image of the second pattern; and
   the first pattern is geometrically identical to the second pattern, or the first pattern and the second pattern are periodic and a pitch of the first pattern is identical to a pitch of the second pattern.

2. The method of clause 1, wherein the second target comprises the second pattern and an optical path, relative to the first target, of the first scattered radiation between the first target and the detector is identical to an optical path, relative to the second target, of the second scattered radiation between the second target and the detector.

3. The method of clause 1, wherein the second target comprises the pupil plane image of the second pattern and an optical path, relative to the pupil plane image of the first target, of the first scattered radiation between the pupil plane image of the first target and the detector is identical to the optical path, relative to the second target, of the second scattered radiation between the second target and the detector.

4. The method of any preceding clause, wherein an outer contour of the first pattern is substantially the same shape, substantially the same size, or substantially the same shape and the same size, as an outer contour of the second pattern.

5. The method of any preceding clause, wherein the second target comprises a spatial light modulator.

6. The method of any preceding clause, further comprising applying a time-varying phase modulation to the second scattered radiation.

7. The method of clause 6, wherein the second target comprises a spatial light modulator and the time-varying phase modulation is applied using the spatial light modulator.

8. The method of clause 6 or 7, further comprising filtering an output from the detector based on a frequency of the phase modulation.

9. The method of any preceding clause, further comprising filtering the second scattered radiation as a function of a signal level of the first scattered radiation in order to control a dynamic range at the detector.

10. A metrology apparatus for inspected a substrate, the metrology apparatus comprising:
    a radiation source configured to provide a source beam of radiation;
    a beam splitter configured to split the source beam of radiation into a measurement beam and a reference beam; and
    an optical system configured to:
    illuminate a first target with the measurement beam, the first target being on the substrate;
    illuminate a second target with the reference beam, the second target being separated from the substrate;
    collect first scattered radiation from the first target and deliver the first scattered radiation to a detector; and
    collect second scattered radiation from the second target and deliver the second scattered radiation to the detector, wherein:
    the optical system is configured such that the second scattered radiation is delivered to the detector in such a way as to interfere with the first scattered radiation at the detector;
    the first target comprises a first pattern;
    the second target comprises a second pattern, or a pupil plane image of the second pattern; and
    the first pattern is geometrically identical to the second pattern, or the first pattern and the second pattern are periodic and a pitch of the first pattern is identical to a pitch of the second pattern.

11. The apparatus of clause 10, wherein the second target comprises the second pattern and the optical system is configured such that an optical path, relative to the first target, of the first scattered radiation between the first target and the detector is identical to an optical path, relative to the second target, of the second scattered radiation between the second target and the detector.

12. The apparatus of clause 10, wherein the second target comprises the pupil plane image of the second pattern and the optical system is configured such that an optical path, relative to the pupil plane image of the first target, of the first scattered radiation between the pupil plane image of the first target and the detector is identical to the optical path, relative to the second target, of the second scattered radiation between the second target and the detector.

13. The apparatus of any of clauses 10-12, wherein an outer contour of the first pattern is substantially the same shape, substantially the same size, or substantially the same shape and the same size, as an outer contour of the second pattern.

14. The apparatus of any of clauses 10-13, wherein the second target comprises a spatial light modulator.

15. The apparatus of any of clauses 10-14, wherein the apparatus is configured to apply a time-varying phase modulation to the second scattered radiation.

16. The apparatus of clause 15, wherein the second target comprises a spatial light modulator and the time-varying phase modulation is applied using the spatial light modulator.

17. The apparatus of clause 15 or 16, wherein the apparatus is configured to filter an output from the detector based on a frequency of the phase modulation.

18. The apparatus of any of clauses 10-17, further comprising a filter system configured to filter the second scattered radiation as a function of a signal level of the first scattered radiation in order to control a dynamic range at the detector.

19. A lithographic system comprising:
a lithographic apparatus configured to perform a lithographic process; and
the metrology apparatus of any of clauses 10-18, wherein:
the lithographic apparatus is arranged to use a result of inspecting a substrate obtained using the metrology apparatus in a lithographic process.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens," where the context allows, may refer to any one or combination of various types of optical components, including refractive, reflective, magnetic, electromagnetic, and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method of inspecting a substrate, the method comprising:
splitting a source beam of radiation emitted by a radiation source into a measurement beam and a reference beam;
illuminating a first target with the measurement beam, the first target being on the substrate;
illuminating a second target with the reference beam, the second target being separated from the substrate;
collecting first scattered radiation from the first target;
delivering the first scattered radiation to a detector;
collecting second scattered radiation from the second target;
delivering the second scattered radiation to the detector, wherein:
the first target comprises a first pattern, and the first scattered radiation includes a first contribution scattered from the first pattern;
the second target comprises a second pattern or a pupil plane image of the second pattern, and the second scattered radiation includes a second contribution scattered from the second pattern or the pupil plane image of the second pattern;
the first pattern is geometrically identical to the second pattern or the first pattern and the second pattern is periodic and a pitch of the first pattern is identical to a pitch of the second pattern; and
the first scattered radiation interferes with the second scattered radiation at the detector, such that noise from contributions other than the first contribution and the second contribution is removed or reduced from a resulting interference pattern at the detector.

2. The method of claim 1, wherein:
the second target comprises the second pattern and an optical path, and
the optical path relative to the first target, of the first scattered radiation between the first target and the detector, is identical to an optical path, relative to the second target, of the second scattered radiation between the second target and the detector.

3. The method of claim 1, wherein:
the second target comprises the pupil plane image of the second pattern and an optical path, and
the optical path, relative to the pupil plane image of the first target, of the first scattered radiation between the pupil plane image of the first target and the detector is identical to the optical path, relative to the second target, of the second scattered radiation between the second target and the detector.

4. The method of claim 1, wherein an outer contour of the first pattern is substantially the same shape, substantially the same size, or substantially the same shape and the same size, as an outer contour of the second pattern.

5. The method of claim 1, wherein the second target comprises a spatial light modulator.

6. The method of claim 1, further comprising applying a time-varying phase modulation to the second scattered radiation.

7. The method of claim 6, further comprising using a spatial light modulator to apply the time-varying phase modulation.

8. The method of claim 6, further comprising performing a lock-in processing to an output from the detector to extract components at a frequency of the time-varying phase modulation.

9. The method of claim 1, further comprising filtering the second scattered radiation as a function of a signal level of the first scattered radiation in order to control a dynamic range at the detector.

10. A metrology apparatus for inspecting a substrate, the metrology apparatus comprising:
   a radiation source configured to provide a source beam of radiation;
   a beam splitter configured to split the source beam of radiation into a measurement beam and a reference beam; and
   an optical system configured to:
      illuminate a first target with the measurement beam, the first target being on the substrate;
      illuminate a second target with the reference beam, the second target being separated from the substrate;
      collect first scattered radiation from the first target and deliver the first scattered radiation to a detector; and
      collect second scattered radiation from the second target and deliver the second scattered radiation to the detector,
   wherein:
      the first target comprises a first pattern, and the first scattered radiation includes a first contribution scattered from the first pattern;
      the second target comprises a second pattern or a pupil plane image of the second pattern, and the second scattered radiation includes a second contribution scattered from the second pattern or the pupil plane image of the second pattern;
      the first pattern is geometrically identical to the second pattern or the first pattern and the second pattern is periodic and a pitch of the first pattern is identical to a pitch of the second pattern; and
      the optical system is configured such that the second scattered radiation is delivered to the detector in such a way as to interfere with the first scattered radiation at the detector, such that noise from contributions other than the first contribution and the second contribution is removed or reduced from a resulting interference pattern at the detector.

11. The apparatus of claim 10, wherein:
   the second target comprises the second pattern; and
   the optical system is configured such that an optical path, relative to the first target, of the first scattered radiation between the first target and the detector is identical to an optical path, relative to the second target, of the second scattered radiation between the second target and the detector.

12. The apparatus of claim 10, wherein:
   the second target comprises the pupil plane image of the second pattern; and
   the optical system is configured such that an optical path, relative to the pupil plane image of the first target, of the first scattered radiation between the pupil plane image of the first target and the detector is identical to the optical path, relative to the second target, of the second scattered radiation between the second target and the detector.

13. The apparatus of claim 10, wherein an outer contour of the first pattern is substantially the same shape, substantially the same size, or substantially the same shape and the same size, as an outer contour of the second pattern.

14. The apparatus of claim 10, wherein the second target comprises a spatial light modulator.

15. The apparatus of claim 14, wherein the apparatus is configured to use the spatial light modulator to apply a time-varying phase modulation to the second scattered radiation.

16. The apparatus of claim 15, wherein the apparatus further comprises a lock-in controller configured to perform a lock-in processing to an output from the detector to extract components at a frequency of the time-varying phase modulation.

17. The apparatus of claim 10, further comprising a filter system configured to filter the second scattered radiation as a function of a signal level of the first scattered radiation in order to control a dynamic range at the detector.

18. A lithographic system comprising:
   a lithographic apparatus configured to perform a lithographic process; and
   a metrology apparatus comprising:
      a radiation source configured to provide a source beam of radiation;
      a beam splitter configured to split the source beam of radiation into a measurement beam and a reference beam; and
      an optical system configured to:
         illuminate a first target with the measurement beam, the first target being on the substrate;
         illuminate a second target with the reference beam, the second target being separated from the substrate;
         collect first scattered radiation from the first target and deliver the first scattered radiation to a detector; and
         collect second scattered radiation from the second target and deliver the second scattered radiation to the detector, wherein:
         the first target comprises a first pattern, and the first scattered radiation includes a first contribution scattered from the first pattern;
         the second target comprises a second pattern or a pupil plane image of the second pattern, and the second scattered radiation includes a second contribution scattered from the second pattern or the pupil plane image of the second pattern; and
         the optical system is configured such that the second scattered radiation is delivered to the detector in such a way as to interfere with the first scattered radiation at the detector, such that noise from contributions other than the first contribution and the second contribution is removed or reduced from a resulting interference pattern at the detector;
      wherein the lithographic apparatus is arranged to use a result of inspecting a substrate obtained using the metrology apparatus in a lithographic process.

* * * * *